United States Patent
Mack et al.

(10) Patent No.: US 11,173,295 B2
(45) Date of Patent: Nov. 16, 2021

(54) DRY DISCONNECT/BUBBLE FREE COUPLING FOR BLOOD TRANSFER

(71) Applicant: HeartWare, Inc., Miami Lakes, FL (US)

(72) Inventors: Stanley P. Mack, Pinellas Park, FL (US); Charles R. Shambaugh, Coral Gables, FL (US)

(73) Assignee: HeartWare Inc., Miami Lakes, FL (US)

( * ) Notice: Subject to any disclaimer, the term of this patent is extended or adjusted under 35 U.S.C. 154(b) by 0 days.

(21) Appl. No.: 16/984,315

(22) Filed: Aug. 4, 2020

(65) Prior Publication Data
US 2020/0360680 A1   Nov. 19, 2020

Related U.S. Application Data

(63) Continuation of application No. 16/149,391, filed on Oct. 2, 2018, now Pat. No. 10,864,364.
(Continued)

(51) Int. Cl.
*A61M 39/26* (2006.01)
*A61M 1/36* (2006.01)
(Continued)

(52) U.S. Cl.
CPC .......... *A61M 39/26* (2013.01); *A61M 1/3638* (2014.02); *A61M 1/3653* (2013.01);
(Continued)

(58) Field of Classification Search
CPC ............ A61M 39/26; A61M 2039/267; A61M 2039/268; A61M 2039/261;
(Continued)

(56) References Cited

U.S. PATENT DOCUMENTS

| 1,857,420 | A | ‡ | 5/1932 | Wolford | ................ F16L 37/252 285/85 |
| 1,968,075 | A | ‡ | 7/1934 | Ewald | ................... F16L 37/252 251/149.5 |

(Continued)

FOREIGN PATENT DOCUMENTS

| EP | 2452720 A1 ‡ | 5/2012 | ........ A61M 39/1011 |
| EP | 2452720 A1 | 5/2012 | |

(Continued)

OTHER PUBLICATIONS

International Search Report and Written Opinion dated Dec. 11, 2018, for corresponding International Application No: PCT/US2018/053893; International Filing Date: Oct. 2, 2018 consisting of 12-pages.‡

*Primary Examiner* — David Colon-Morales
(74) *Attorney, Agent, or Firm* — Christopher & Weisberg, P.A.

(57) ABSTRACT

A dry disconnect device including a first portion defining an outlet and an outlet portion of a fluid pathway and a female valve disposed within the first portion having an extended position, including the female valve being configured to seal the outlet portion, and a retracted position. A second portion defining an inlet and an inlet portion of the fluid pathway is lockingly engageable with the first portion. A male valve is disposed within the second portion including a male valve transition member configured to translate the male valve from an extended position to a retracted position including the male valve being configured to seal the inlet portion. The extended position of the male valve causes the female valve to transition from the extended position to the retracted position and causes the outlet portion and the inlet portion of the fluid pathway to be in fluid communication with each other.

14 Claims, 8 Drawing Sheets

Related U.S. Application Data

(60) Provisional application No. 62/570,733, filed on Oct. 11, 2017.

(51) Int. Cl.
*F16L 37/244* (2006.01)
*F16L 37/36* (2006.01)

(52) U.S. Cl.
CPC .............. *F16L 37/244* (2013.01); *F16L 37/36* (2013.01); *A61M 2039/267* (2013.01); *A61M 2039/268* (2013.01)

(58) Field of Classification Search
CPC ...... A61M 2039/262; A61M 2039/263; A61M 2039/265; A61M 2039/266; A61M 39/22; A61M 1/3653; A61M 1/3621; A61M 1/3638; F16L 37/30; F16L 37/36; F16L 37/24; F16L 37/244; F16L 37/252; F16L 37/256

See application file for complete search history.

(56) References Cited

U.S. PATENT DOCUMENTS

| | | | | |
|---|---|---|---|---|
| 2,203,922 A ‡ | 6/1940 | Paisley | ................... | F16L 37/36 137/614.06 |
| 3,474,827 A ‡ | 10/1969 | Rosell | .................... | F16L 37/36 137/614.03 |
| 4,271,865 A ‡ | 6/1981 | Galloway | ............. | F16L 37/101 137/614.06 |
| 4,610,469 A ‡ | 9/1986 | Wolff-Mooij | ......... | A61M 39/26 285/260 |
| 4,921,013 A ‡ | 5/1990 | Spalink | .................... | F16L 37/30 137/614.01 |
| 5,009,252 A ‡ | 4/1991 | Faughn | ................. | F16L 37/113 137/614.04 |
| 5,143,346 A ‡ | 9/1992 | Chen | ......................... | E03B 7/09 137/322 |
| 5,211,197 A ‡ | 5/1993 | Marrison | ................ | F16L 37/23 137/61 |
| 5,396,927 A ‡ | 3/1995 | Marshall | ................. | F16L 37/36 137/614.06 |
| 5,404,909 A ‡ | 4/1995 | Hanson | ................. | F16L 37/113 137/614.06 |
| 5,492,147 A ‡ | 2/1996 | Challender | ........... | F16L 29/005 137/61 |
| 5,671,777 A ‡ | 9/1997 | Allen | ....................... | F16L 37/36 137/614.06 |
| 5,887,619 A ‡ | 3/1999 | Keary | .................... | F16K 15/063 137/614.18 |
| 7,128,091 B2 ‡ | 10/2006 | Istre, Jr. | ................. | F16L 37/252 137/515.5 |
| 7,922,148 B2 ‡ | 4/2011 | Walborn | ............... | A61M 39/26 251/128 |
| 8,926,591 B2 ‡ | 1/2015 | Schutz | ............... | A61M 39/0247 604/174 |
| 9,909,703 B2 ‡ | 3/2018 | Van Scyoc | ............. | F16L 37/32 |
| 10,864,364 B2 * | 12/2020 | Mack | ................... | A61M 1/3653 |
| 2009/0043253 A1 ‡ | 2/2009 | Podaima | ................ | G16H 10/60 604/67 |
| 2010/0019485 A1 ‡ | 1/2010 | Huegerich | .............. | F16L 37/62 285/119 |
| 2015/0258324 A1 ‡ | 9/2015 | Chida | .................... | A61M 39/10 604/53 |
| 2015/0276111 A1 ‡ | 10/2015 | Ira | ........................... | F16L 37/32 137/61 |
| 2018/0161568 A1 ‡ | 6/2018 | Banco | .................... | A61M 39/18 |
| 2019/0086015 A1 ‡ | 3/2019 | Tarissan | ................ | F16L 29/007 |

FOREIGN PATENT DOCUMENTS

| | | | | |
|---|---|---|---|---|
| WO | 2006078355 A1 | 7/2006 | | |
| WO | WO-2006078355 A1 ‡ | 7/2006 | ............. | F16L 29/04 |
| WO | 2013153722 A1 | 10/2013 | | |
| WO | WO-2013153722 A1 ‡ | 10/2013 | ........ | A61M 39/1011 |

\* cited by examiner
‡ imported from a related application

DRY DISCONNECT/BUBBLE FREE COUPLING FOR BLOOD TRANSFER

CROSS-REFERENCE TO RELATED APPLICATION

This application is a continuation of U.S. Utility application Ser. No. 16/149,391, filed Oct. 2, 2018, and claims the benefit of U.S. Application Ser. No. 62/570,733, filed Oct. 11, 2017, the entirety of which is incorporated herein by reference.

FIELD

The present technology is generally related a dry disconnect device for transferring blood between a patient and an external device.

BACKGROUND

Extracorporeal medical procedures include transferring blood outside of a patient's body using one or more fluid transfer tubes, such as catheters, connected to the patient and a machine to establish a continuous fluid pathway therebetween. For example, extracorporeal membrane oxygenation ("ECMO") machines pump and oxygenate the patient's blood from outside of the patient's body and thereafter return the oxygenated blood to the patient's body. The tubes and/or the machine must be carefully connected to each other as the introduction of air bubbles into the fluid pathway increases the risk of death or medical complications, such as thrombus.

Various systems and devices have been developed to connect fluid transfer tubes to each other. However, such systems and devices are complicated to use, consume a relatively large amount of space, and are of a size and shape prone to creating thrombus. Existing devices, such as dry disconnect couplings, are configured to connect and disconnect the fluid transfer tubes, however, such devices are susceptible to leakage and creating hazardous air bubbles. Still, other devices don't allow for connecting and disconnecting the fluid transfer tubes following a first initial connection. As a further drawback, known systems and devices are not equipped with various safety features, such as a safety lock and/or status indicator, to indicate the status of fluid transfer.

SUMMARY

The techniques of this disclosure generally relate to a dry disconnect device configured to transfer blood from a patient to an external device without introducing air bubbles into the device.

In one aspect, the present disclosure provides a dry disconnect device including a first housing and a second housing lockingly engageable with each other and defining a fluid pathway therebetween; a female valve disposed within the first housing and having an extended position including the female valve sealing the fluid pathway and a retracted position including the female valve outside of the fluid pathway; a male valve disposed within the second housing and having an extended position including the male valve outside of the fluid pathway and a retracted position when the female valve is in the extended position, the retracted position including the male valve sealing the fluid pathway; and a male valve transition member in communication with the male valve for transitioning the male valve from the retracted position to the extended position when the first housing is locked to the second housing, the extended position of the male valve causing the female valve to transition from the extended position to the retracted position and causing the fluid pathway between the first housing and the second housing to be in fluid communication.

In another aspect, the disclosure provides the first housing defining an outlet and an outlet portion of the fluid pathway, and the female valve seals the outlet portion of the fluid pathway when the female valve is in the extend position.

In another aspect, the disclosure provides the second housing defining an inlet and an inlet portion of the fluid pathway, and the male valve includes a proximal portion and a distal portion opposite the proximal portion, the proximal portion translating from the second housing into the first housing when the male valve is in the extended position.

In another aspect, the disclosure provides the proximal portion of the male valve being sized to seal the inlet portion of the fluid pathway.

In another aspect, the disclosure provides the dry disconnect device including a gasket surrounding the proximal portion of the male valve.

In another aspect, the disclosure provides the male valve transition member being a biasing member coupled to the distal portion of the male valve, and the second housing includes a rotatable fastener coupled to the male valve transition member.

In another aspect, the disclosure provides the dry disconnect device including a female valve transition member coupled to the female valve.

In another aspect, the disclosure provides the first housing including a shoulder having a smooth outer surface, and the female valve is coupled to the shoulder when the female valve is in the retracted position.

In another aspect, the disclosure provides the fluid pathway being continuous and uninterrupted when the female valve is in the retracted position and the male valve is in the extended position.

In another aspect, the disclosure provides the female valve and the male valve forming an air tight seal when coupled to each other.

In another aspect, the disclosure provides the dry disconnect device including a locking member including a base and a moveable member, the base coupled to the second housing and the moveable member lockingly engageable with the first housing.

In another aspect, the disclosure provides the dry disconnect device including a position sensor in communication with at least one of a group consisting of the female valve and the male valve.

In another aspect, the disclosure provides the first housing and the second housing being lockingly engaged to each other when the position sensor determines that the male valve is coupled to the female valve.

In one aspect, the present disclosure provides a dry disconnect device including a first housing defining an outlet, a first aperture, and an outlet portion of a fluid channel extending between the outlet and the first aperture; a first valve disposed within the first housing, the first valve having a closed position including the first valve disposed within and sealing the outlet portion of the fluid channel and an open position including the first valve disposed outside of the outlet portion of the fluid channel; a second housing removably couplable to the first housing, the second housing defining an inlet, a second aperture, and an inlet portion of the fluid channel extending between the inlet and the second aperture; and a second valve disposed within the second housing, the second valve having a closed position including the second valve disposed within and sealing the inlet portion of the fluid channel and an open position including the first housing being coupled to the second housing and the second valve being inserted within the first housing to cause the outlet portion and the inlet portion of the fluid channel to be in fluid communication with each other.

In another aspect, the disclosure provides the second valve including a proximal portion and a distal portion opposite the proximal portion, the proximal portion being insertable within the first housing and having a shape complimentary to a shape of the first valve.

In another aspect, the disclosure provides the second aperture being sized to receive the proximal portion of the second valve therein to seal the inlet portion of the fluid channel.

In another aspect, the disclosure provides the dry disconnect device including a male valve transition member coupled to the distal portion of the second valve.

In another aspect, the disclosure provides the dry disconnect device including a locking member coupled to at least one of a group consisting of the first housing and the second housing.

In another aspect, the disclosure provides the dry disconnect device including a position sensor coupled to at least one of a group consisting of the first housing and the second housing, the position sensor in communication with the locking member.

In one aspect, the present disclosure provides a dry disconnect device including a first portion defining an outlet and a first portion of a fluid pathway in fluid communication with the outlet; a female valve disposed within the first portion, the female valve having an extended position and a retracted position and being configured to seal the first portion of the fluid pathway in the extended position; a second portion lockingly engageable with the first portion, the second portion defining an inlet and a second portion of the fluid pathway in communication with the inlet; a male valve disposed within the second portion, the male valve having a proximal portion and a distal portion opposite the proximal portion; an extended position; and a retracted position, the proximal portion of the male valve being configured to seal the second portion of the fluid pathway in the retracted position; a male valve transition member coupled to the distal portion of the male valve, the male valve transition member being configured to transition the male valve from the retracted position to the extended position when the first portion is coupled to the second portion, the extended position of the male valve including the proximal portion being inserted within the first portion to cause the female valve to transition from the extended position to the retracted position and to cause the first portion of the fluid pathway and the second portion of the fluid pathway to be in fluid communication with each other; and a locking member coupled to at least one of a group consisting of the first portion and the second portion.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
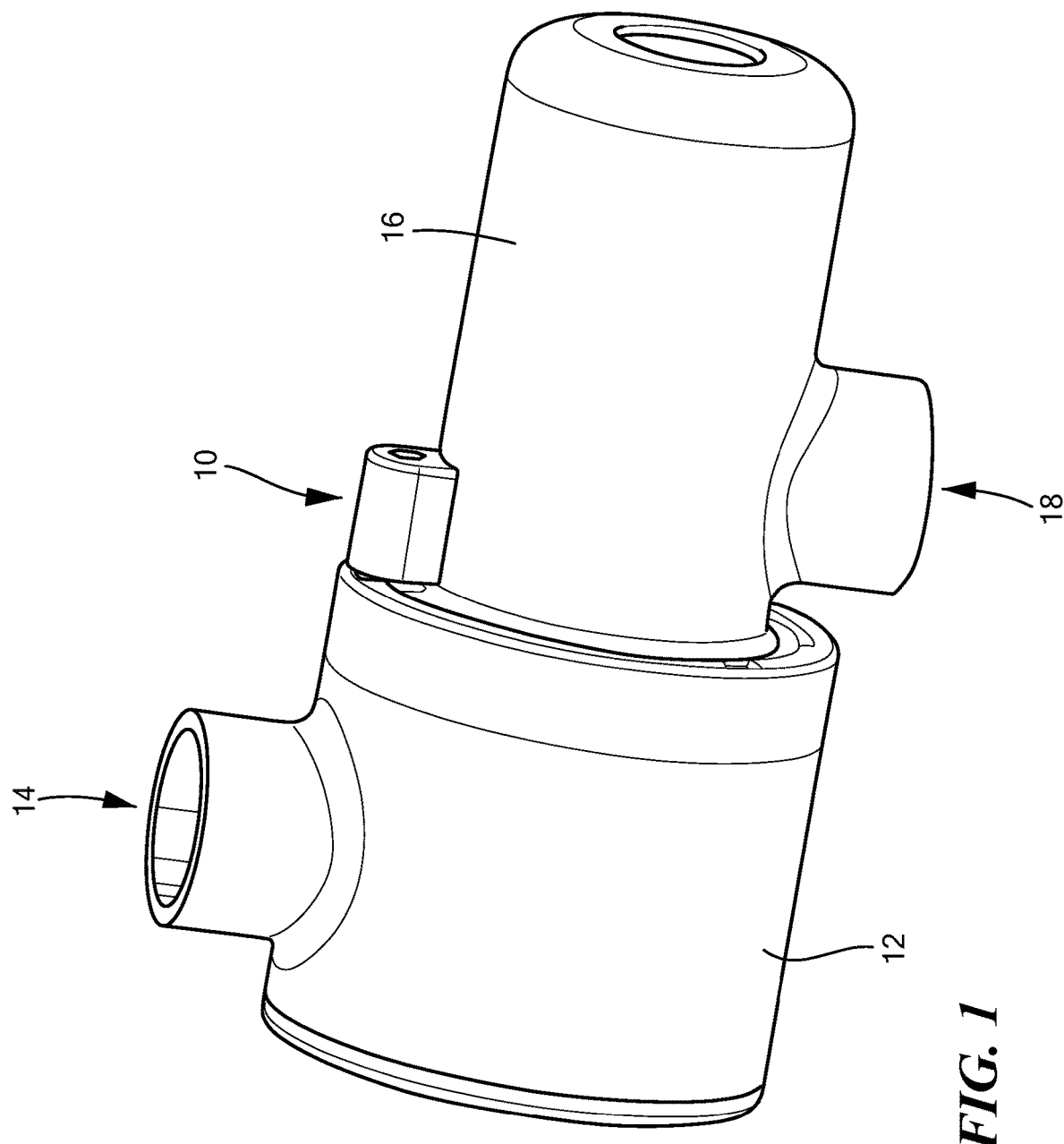
FIG. 1 is a perspective view of a dry disconnect device that illustrates the dry disconnect device including a first housing and a second housing coupled to each other and defining an outlet and in inlet.

Before describing in detail exemplary embodiments, it is noted that the embodiments reside primarily in combinations of device and apparatus components and processing steps related to a dry disconnect device. Accordingly, the device, apparatus, and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Figure 2:
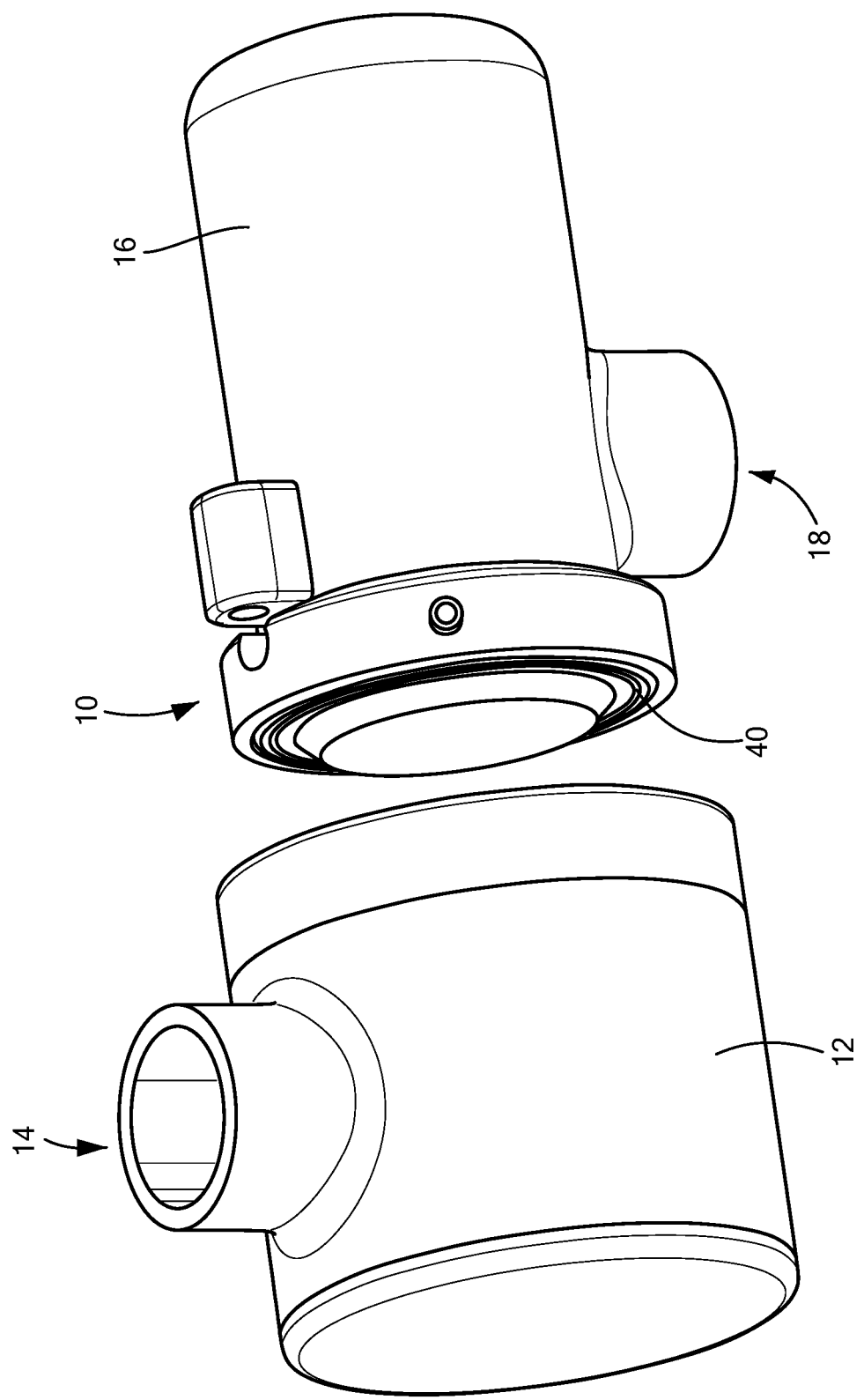
FIG. 2 is a perspective view of the dry disconnect device of FIG. 1 that illustrates the first housing and the second housing separated from each other.
Figure 3:
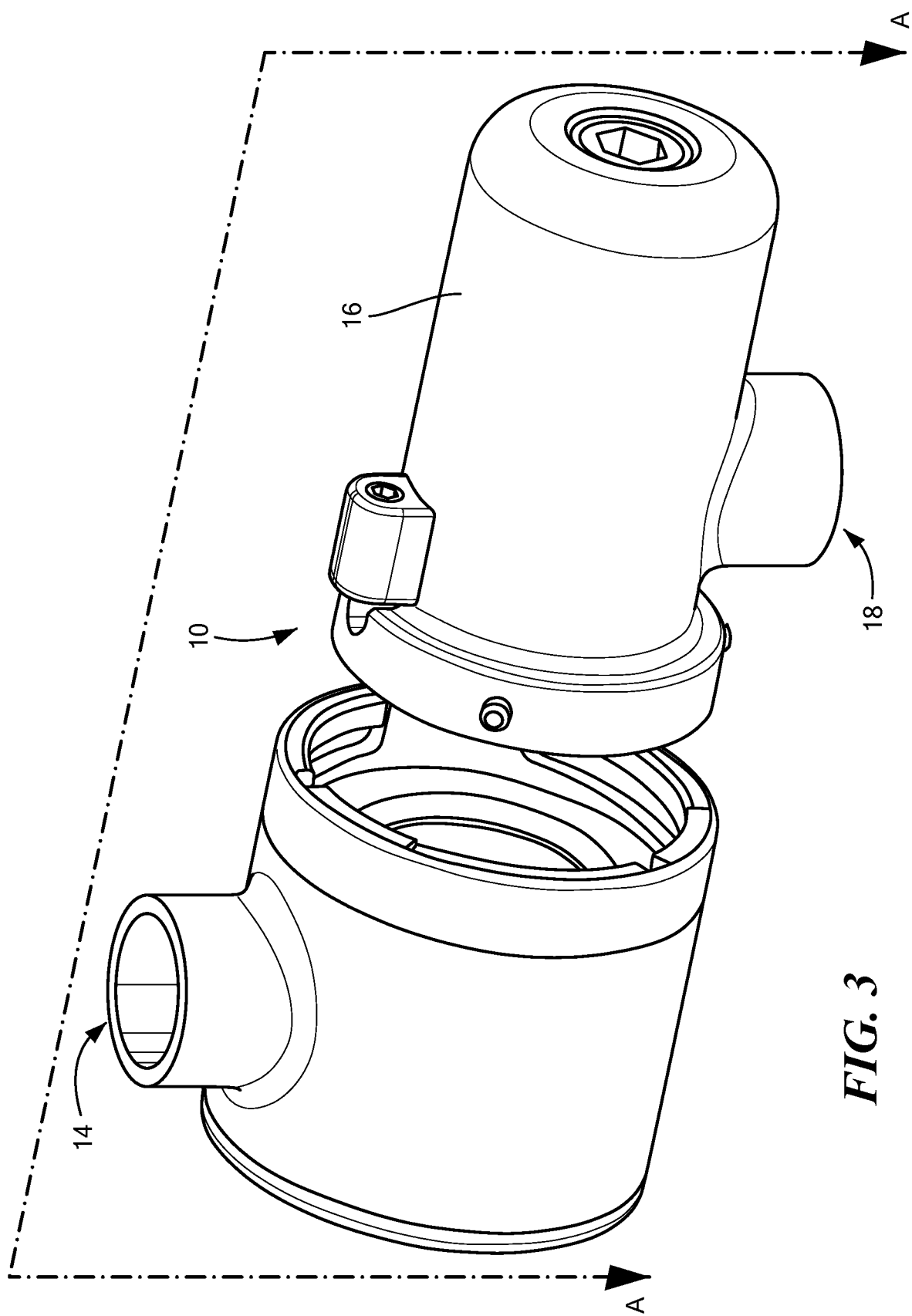
FIG. 3 is a perspective view of the dry disconnect device of FIG. 1 that illustrates the first housing and the second housing separated from each other and the first housing including a female valve disposed therein.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein Referring now to the drawings in which like reference designators refer to like elements there is shown in FIG. 1 an exemplary dry disconnect device constructed in accordance with the principles of the present application and designated generally "10." The dry disconnect device 10 is configured to lock and transfer blood from a patient to an external device without the risk of air bubbles entering the device 10. FIG. 1 depicts the device 10 including a first housing 12 defining an outlet 14 and a second housing 16 defining an inlet 18 for fluid to travel from the inlet 18 to the outlet 14. The second housing 16 is lockingly engageable with the first housing 12. FIG. 1 depicts the housings 12 and 16 locked together, whereas FIGS. 2 and 3 depict the housings 12 and 16 uncoupled or separated from each other. The first housing 12 and the second housing 16 include an interior made of biocompatible materials, such as stainless steel, titanium, composite, ceramic, silicone, or the like with the second housing 16 being configured to connect to a patient for an extended time period, such as weeks, months, or years.

Figure 4:
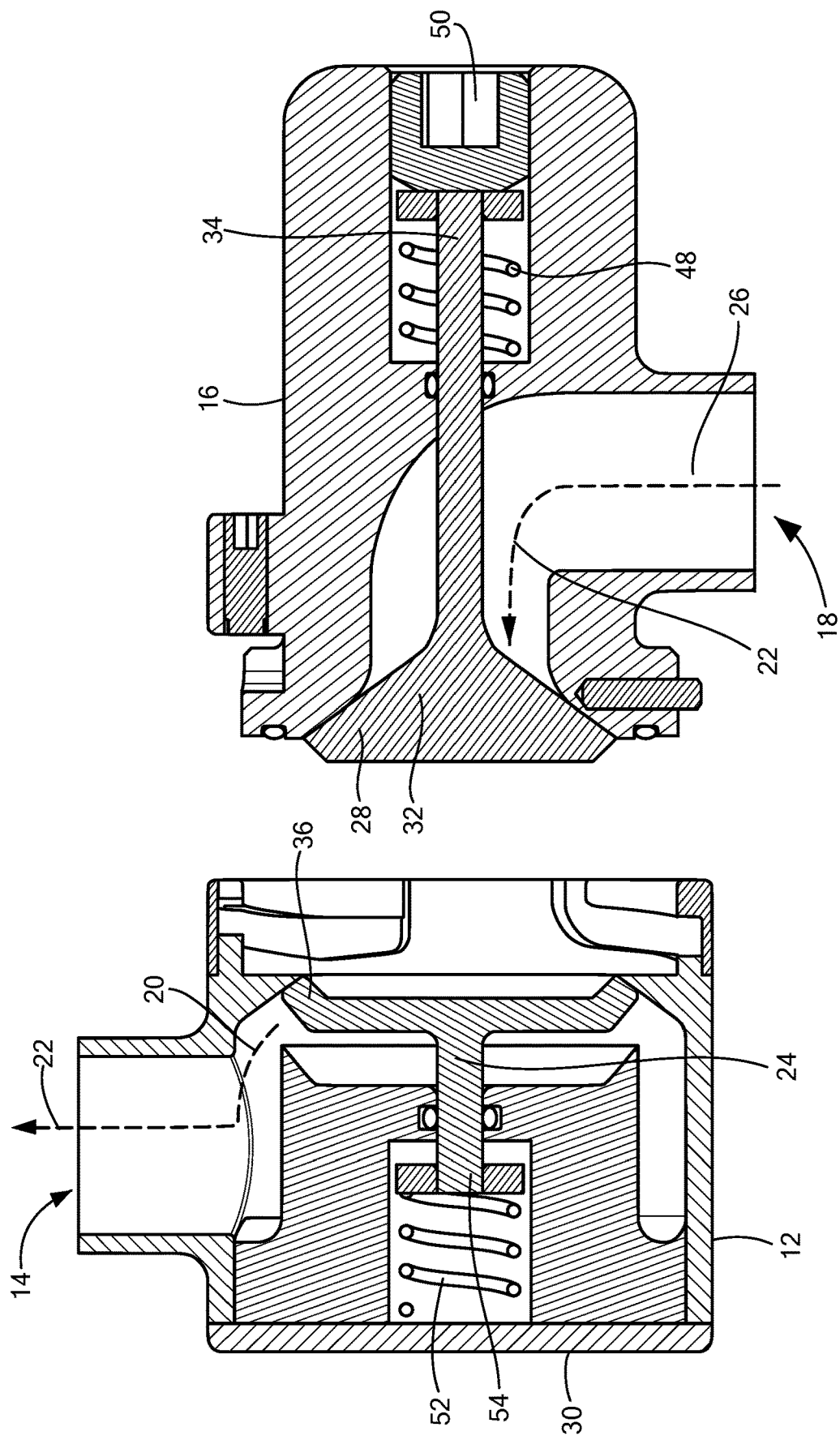
FIG. 4 is a cross-sectional side view of the dry disconnect device taken along section A-A of FIG. 3 that illustrates the first housing including the female valve and the second housing including a male valve with both valves being in a closed position sealing a fluid pathway between the first housing and the second housing.

FIG. 4 is a cross-sectional side view of the device 10 taken along section A-A of FIG. 3. The first housing 12 defines an outlet portion 20 of a fluid pathway 22 in fluid communication with the outlet 14 and extending through the first housing 12. A first valve or female valve 24 is disposed within the first housing 12 to selectively seal the outlet portion 20 of the fluid pathway 22, which may also be referred to as a channel. The second housing 16 defines an inlet portion 26 of the fluid pathway 22 in communication with the inlet 18 and extending through the second housing 16. As such, the inlet portion 26 and the outlet portion 20 collectively define the fluid pathway 22 through the device 10 to transfer blood from the patient to an external device (not shown). A second valve or male valve 28 is disposed within the second housing 16 for selectively sealing the inlet portion 26 of the fluid pathway 22.

The female valve 24 and the male valve 28 selectively seal the fluid pathway 22 by moving in and out of the fluid pathway 22. For example, FIG. 4 depicts the female valve 24 including an extended or closed position in which the female valve 24 extends away from a rear wall 30 and within the fluid pathway 22 to seal the outlet portion 20. The male valve 28 is depicted in a retracted or closed position within the second housing 16 and uncoupled from the female valve 24 to seal the inlet portion 26 of the fluid pathway 22.

Figure 5:
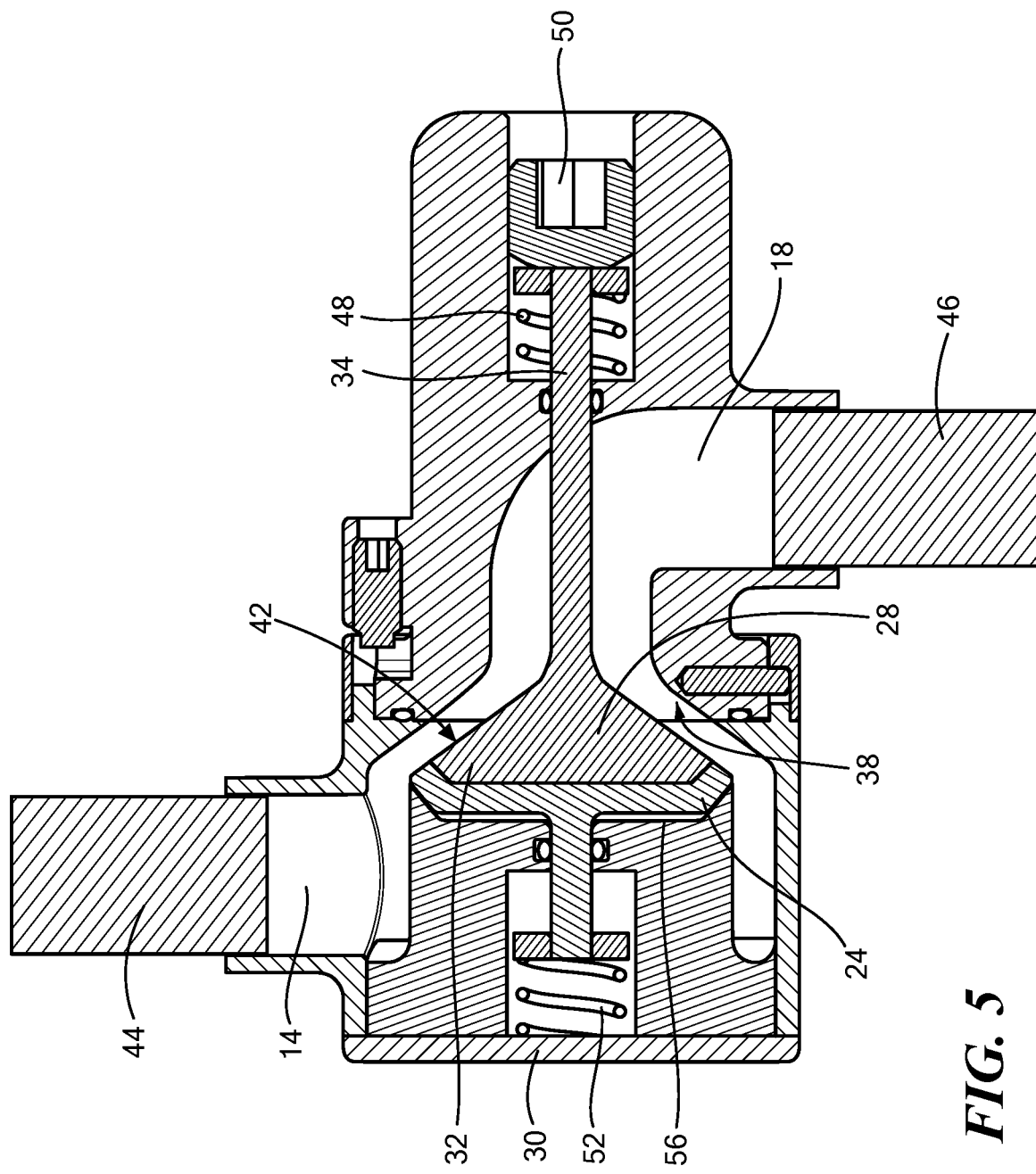
FIG. 5 is a cross-sectional side view of the dry disconnect device of FIG. 1 that illustrates the female valve and the male valve in an open position defining a continuous fluid pathway between the first housing and the second housing.

FIG. 5 depicts the opposite configurations with respect to FIG. 4, namely the female valve 24 including a retracted or open position in which the female valve 24 retracts within the first housing 12 toward the rear wall 30 and outside of the fluid pathway 22. In addition, the male valve 28 is in the extended position in which the male valve 28 extends into the first housing 12 to contact the female valve 24 and transition the female valve 24 from the closed position to the open position. In other words, the male valve 28 forces the female valve 24 toward the rear wall 30 of the first housing 12 to move the female valve 24 and the male valve 28 outside of the fluid pathway 22. Once the female valve 24 is retracted outside of the fluid pathway 22, the outlet portion 20 and the inlet portion 26 of the fluid pathway 22 are open and caused to be in fluid communication with each other.

FIGS. 4 and 5 depict the male valve 28 including a proximal portion 32 and a distal portion 34 opposite the proximal portion 32 with the proximal portion 32 being that which is inserted within the first housing 12. The proximal portion 32 may be circular or another shape that is complimentary to a shape of a proximal portion 36 of the female valve 24. As such, the proximal portion 32 of the male valve 28 and the proximal portion 36 of the female valve 24 may be pressed together to form a fluid and/or air tight seal therebetween. The shape of the male valve 28 is also sized to seal the fluid pathway 22 and an aperture 38 (FIG. 5) defined by the second housing 16 which allows fluid to flow outside of the second housing 16 into the first housing 12 when the device 10 is activated. FIG. 2 depicts a gasket 40 surrounding the proximal portion 32 of the male valve 28 to further prevent leakage of fluid between the male valve 28 and the second housing 16 when the male valve 28 is in the closed position. The first housing 12 defines an aperture 42 which aligns with the aperture 38 to allow fluid to flow from the second housing 16 into the first housing 12.

In one configuration, safety of the device 10 is increased through the male valve 28 being placed in the extended position after confirming that the first housing 12 is coupled to the second housing 16 to from a fluid tight seal therebetween. For example, FIG. 5 depicts the device 10 in use including an outlet tube 44 disposed within the outlet 14 and an inlet tube 46 disposed within the inlet 18. The outlet tube 44 may extend to an external device with the inlet tube 46 being coupled to the patient. Blood may be transferred from the patient through the device 10 to the external device without the risk of air bubbles entering the fluid pathway 22 as the entire device 10 is sealed with the only openings being the inlet 18 and the outlet 14. In other words, blood travels through the device 10 from the inlet 18 to the outlet 14 without exposure to air.

FIGS. 4 and 5 depict the device 10 including a male valve transition member 48 coupled to the distal portion 34 of the male valve 28 to transition the male valve 28 from the closed position to the open position. In one configuration, the male valve transition member 48 is a biasing member, such as a spring, coupled to a rotatable fastener 50, such as a hex nut, screw, or the like. Rotation of the rotatable fastener 50 moves the male valve transition member 48 to bias the male valve 28 proximally toward the first housing 12. In the alternative, the male valve transition member 48 may be a solenoid or another electromagnet allowing for electrical operation and manipulation of the male valve 28. Such examples are not intended to be limiting.

In one configuration, a female valve transition member 52, such as a spring, may be coupled to a distal end 54 of the female valve 24. In use, the male valve 28 pushing against the female valve 24 causes the female valve 24 to retract against the female valve transition member 52 to counter the force of the male valve transition member 48. The counter force maintains the fluid and/or air tight seal between the female valve 24 and the male valve 28. In other configurations, the female valve transition member 52 may be another mechanical or a magnetic component configured to counter the force of the male valve transition member 48.

Figure 6:
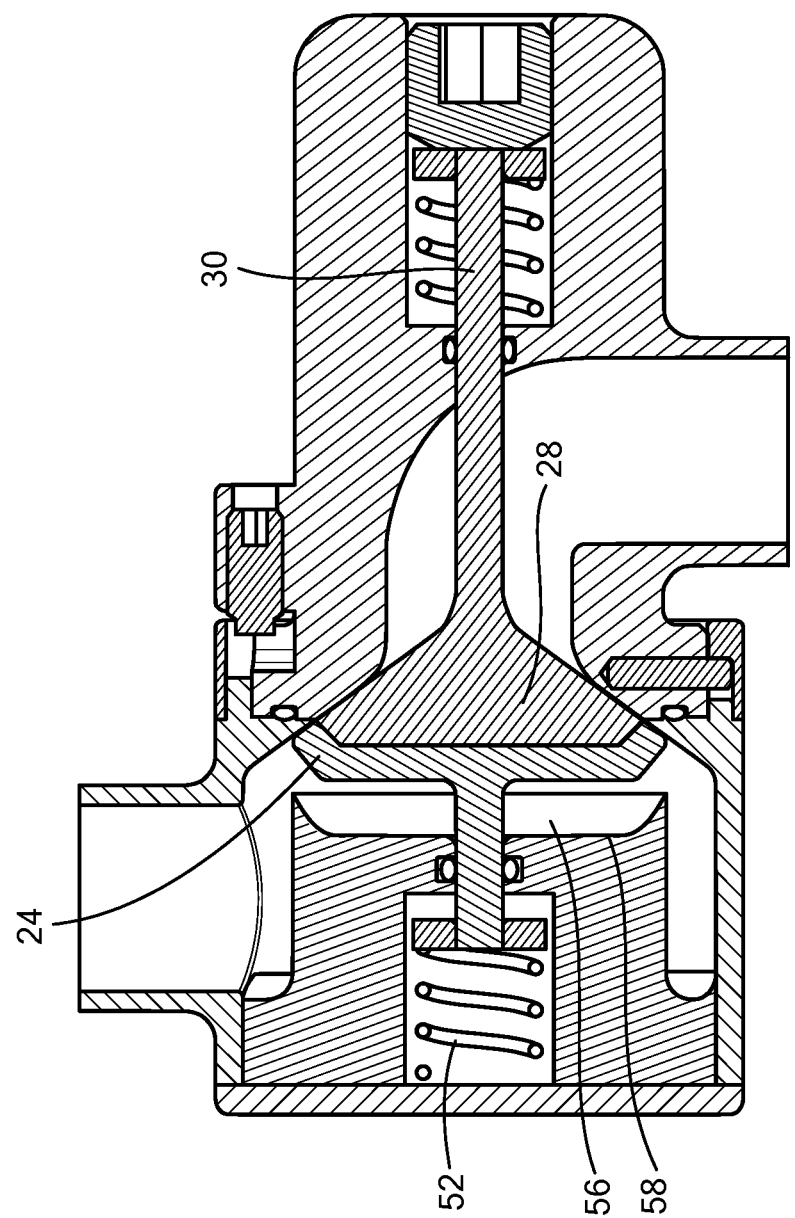
FIG. 6 is a cross-sectional side view of the dry disconnect device of FIG. 1 that illustrates the female valve and the male valve in the closed position sealing the fluid pathway.

FIGS. 5 and 6 depict the first housing 12 including a shoulder 56 for receiving the female valve 24 in contact therewith. For example, FIG. 5 depicts the female valve 24 in the open position including the female valve 24 resting firmly on the shoulder 56. The shoulder 56 may include a smooth outer surface 58 to promote blood flow through the fluid pathway 22 and decrease the risk of thrombus or blood becoming stagnate within the fluid pathway 22.

Figure 7:
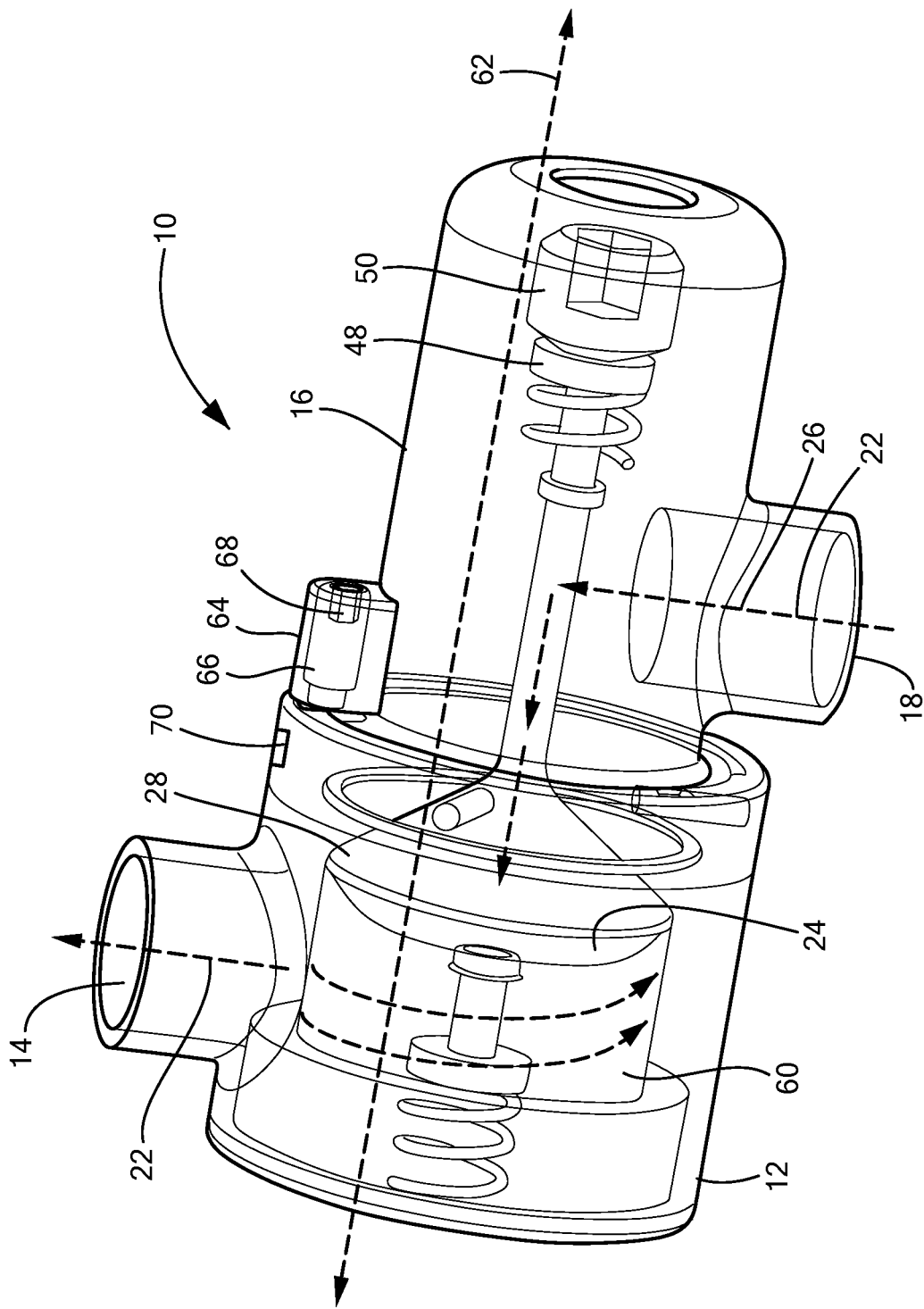
FIG. 7 is a transparent perspective view of the dry disconnect device of FIG. 1 that illustrates a fluid flow path between the first housing and the second housing.

FIG. 7 depicts a transparent perspective view of the device 10 including the fluid pathway 22 being continuous and uninterrupted when the outlet portion 20 and the inlet portion 26 are in fluid communication with each other. The continuous and uninterrupted fluid pathway 22 promotes blood flow and decreases the risk of thrombus within the device 10. In other words, fluid, such as blood, flows freely through the fluid pathway 22 without obstructions and/or turbulence. For example, FIG. 7 depicts the device 10 including the female valve 24 disposed within a cylindrical housing member 60. The cylindrical housing member 60 is free of protrusions and creates a barrier between the female valve 24 and blood flowing through the device 10 during transfer. The remaining portions of the device 10 which define the fluid pathway 22 are also free of protrusions, sharp edges, and the like, known to cause thrombus, shear stress, or other types of blood damage. In configurations not including the cylindrical housing member 60, the smooth outer surface 58 of the shoulder 56 also reduces the risk of thrombus and/or other types of blood damage.

The device 10 defines a device axis 62 extending through the first housing 12 and the second housing 16. The inlet 18 and the outlet 14 are depicted as being transverse to the device axis 62 with the fluid flow pathway 22 being through the inlet 18 and subsequently parallel to the device axis 62 to the first housing 12 where the fluid may flow in a circumferential direction around the female valve 24 to the outlet 14.

The device 10 includes a locking member 64 which locks the first housing 12 and the second housing 16 together during use of the device 10. The locking member 64 may be coupled to either or both housings 12 and 16. In one exemplary configuration, the locking member 64 includes a base 66 and a moveable member 68, such as a pin, lever, handle, or the like, inserted within the base 66 through manual, device, or system activation, such as using an electrical solenoid.

A local or remote position sensor 70 is proximate the locking member 64 and may be coupled to either or both housings 12 and 16. The position sensor 70 may be an accelerometer, resistance-based sensor, capacitive sensor, optical sensor, or the like, in communication with either or both valves 24 and 28 to measure and/or detect a position of the valves 24 and 28 with respect to the fluid pathway 22. Such information indicates the status of the mechanical state of operation, such as whether the fluid pathway 22 is obstructed or open. The remote position sensor 70 may communicate the measurement or position information associated with the first valve 24 and/or the second valve 28 visually through a display, audibly through a speaker, or the like through the device 10. In the alternative, such information may be transmitted to a remote device 10 having a processor in communication with the device 10 through a wired or wireless link. The fluid pathway 22 being open indicates that the device 10 should remain locked and it is safe to transfer fluid through the device 10. For example, with respect to FIG. 7, the position sensor 70 is configured to detect that the first housing 12 and the second housing 16 are lockingly engaged with respect to each other, the male valve 28 is coupled to the female valve 24, and the outlet portion 20 and the inlet portion 26 of the fluid pathway 22 are in communication with each other. As such, the open fluid pathway 22 indicates that it is safe to transfer fluid through the device 10 without the risk of air bubbles entering the device or leakage of fluid.

Figure 8:
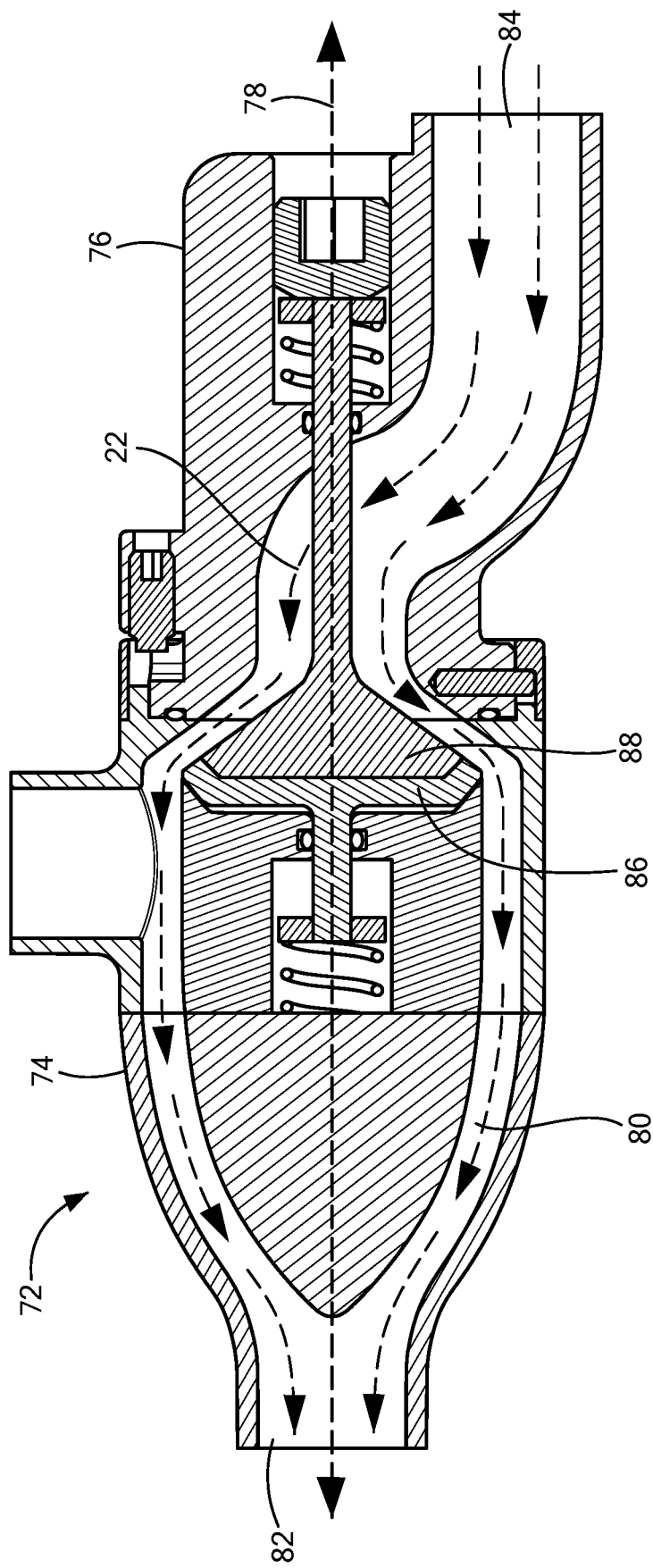
FIG. 8 is a cross-sectional side view of another configuration of a dry disconnect device that illustrates a first housing and a second housing coupled to each other and having a fluid flow path therethrough.

FIG. 8 is a cross-sectional side view of another embodiment of a dry disconnect device 72 including a first housing 74 and a second housing 76 defining a device axis 78 and a fluid pathway 80 extending therethrough. The first housing 74 defines an outlet 82 and the second housing 76 defines an inlet 84 for the fluid pathway 80. The outlet 82 and the inlet 84 are positioned parallel to the device axis 78. In addition, a portion of the fluid pathway 80 is parallel to the device axis 78 with the exception of a curved or angled portion around a female valve 86 and a male valve 88. The dry disconnect device 72 operates in a manner the same as or similar to the dry disconnect device 10 with the outlet 82, the inlet 84, and the fluid pathway 80 being in different locations with respect to the device 10.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A dry disconnect device, comprising:
   a first housing and a second housing lockingly engageable with each other and defining a fluid pathway therebetween;
   a female valve disposed within the first housing and having an extended position including the female valve sealing the fluid pathway and a retracted position including the female valve outside of the fluid pathway;

a male valve disposed within the second housing and having an extended position including the male valve outside of the fluid pathway and a retracted position when the female valve is in the extended position, the retracted position including the male valve sealing the fluid pathway; and a first biasing member in communication with the male valve and a rotatable fastener, the first biasing member being configured to transition the male valve from the retracted position to the extended position when the first housing is locked to the second housing and the rotatable fastener is rotated, the extended position of the male valve causing the female valve to transition from the extended position to the retracted position and causing the fluid pathway between the first housing and the second housing to be in fluid communication.

2. The device of claim 1, wherein the first housing defines an outlet and an outlet portion of the fluid pathway, and the female valve seals the outlet portion of the fluid pathway when the female valve is in the extend position.

3. The device of claim 1, wherein the second housing defines an inlet and an inlet portion of the fluid pathway, and the male valve includes a proximal portion and a distal portion opposite the proximal portion, the proximal portion translating from the second housing into the first housing when the male valve is in the extended position.

4. The device of claim 3, wherein the proximal portion of the male valve is sized to seal the inlet portion of the fluid pathway.

5. The device of claim 4, further comprising a gasket surrounding the proximal portion of the male valve.

6. The device of claim 4, wherein the first biasing member is coupled to the distal portion of the male valve.

7. The device of claim 1, further comprising a second biasing member coupled to the female valve.

8. The device of claim 1, wherein the first housing includes a shoulder having a smooth outer surface, and the female valve is coupled to the shoulder when the female valve is in the retracted position.

9. The device of claim 1, wherein the fluid pathway is continuous and uninterrupted when the female valve is in the retracted position and the male valve is in the extended position.

10. The device of claim 1, wherein the female valve and the male valve form an air tight seal when coupled to each other.

11. The device of claim 1, further comprising a locking member including a base and a moveable member, the base coupled to the second housing and the moveable member lockingly engageable with the first housing.

12. The device of claim 11, further comprising a position sensor in communication with at least one of a group consisting of the female valve and the male valve.

13. The device of claim 12, further comprising the first housing and the second housing being lockingly engaged to each other when the position sensor determines that the male valve is coupled to the female valve.

14. A dry disconnect device, comprising:
a first portion defining an outlet and a first portion of a fluid pathway in fluid communication with the outlet;
a female valve disposed within the first portion, the female valve having an extended position and a retracted position and being configured to seal the first portion of the fluid pathway in the extended position;
a second portion lockingly engageable with the first portion, the second portion defining an inlet and a second portion of the fluid pathway in communication with the inlet;
a male valve disposed within the second portion, the male valve having:
a proximal portion and a distal portion opposite the proximal portion;
an extended position; and
a retracted position, the proximal portion of the male valve being configured to seal the second portion of the fluid pathway in the retracted position;
first biasing member coupled to the distal portion of the male valve, the first biasing member being in communication with a rotatable fastener and configured to transition the male valve from the retracted position to the extended position when the first portion is coupled to the second portion, the extended position of the male valve including the proximal portion being inserted within the first portion to cause the female valve to transition from the extended position to the retracted position and to cause the first portion of the fluid pathway and the second portion of the fluid pathway to be in fluid communication with each other; and
a locking member coupled to at least one of a group consisting of the first portion and the second portion.

* * * * *